US00PP14362P29

(12) United States Plant Patent
Odom

(10) Patent No.: US PP14,362 P2
(45) Date of Patent: Dec. 9, 2003

(54) AZALEA PLANT NAMED 'CRIMSON MAJESTY'

(50) Latin Name: *Rhododendron indicum*
Varietal Denomination: Crimson Majesty

(76) Inventor: Richard Odom, 480 Butter Cemetery Rd., Forest Hill, LA (US) 71430

( * ) Notice: Subject to any disclaimer, the term of this patent is extended or adjusted under 35 U.S.C. 154(b) by 0 days.

(21) Appl. No.: 09/930,573

(22) Filed: Aug. 15, 2001

(51) Int. Cl.[7] ..... A01H 5/00
(52) U.S. Cl. ..... Plt./240
(58) Field of Search ..... Plt./240, 238

*Primary Examiner*—Kent Bell
(74) *Attorney, Agent, or Firm*—Jones, Walker, Waechter, Poitevent, Carrere & Denegre, LLP

(57) ABSTRACT

A new and distinct variety of Azalea which originated as a branch sport of Azalea 'Red Formosa'. The new variety possesses a unique red foliage 187-A, 187-B grayed purple group, and is of full indica size.

15 Drawing Sheets

BACKGROUND OF THE INVENTION

The present invention relates to a new and distinct variety of evergreen azalea, botanically known as *Rhododendron indicum.* Richard Odom discovered this new azalea variety, hereinafter referred to as 'Crimson Majesty', as a naturally occurring branch sport of Azalea 'Red Formosa' at Country Pines Nursery, Inc. in Forest Hill, La. 'Red Formosa' is an unpatented azalea that is well-know in the trade in zones 7–9.

After several generations of asexual propagations through rooting cuttings, the present plant has been developed with its unique foliage coloration and full size, having similar growth patterns and bloom characteristics of the parent plant, 'Red Formosa'.

The selection process focused on foliage color and type of growth rather than on bloom characteristics.

Asexual propagation of the new plant by rooting cuttings has been under Mr. Odom's direction at the same location. Several generations of the new plant have been evaluated and the distinctive characteristics of the plant have remained stable. The plant cannot be reproduced true from seed.

Plant cuttings are allowed to root and grow in a 2.25 inch diameter (rosecup) container for 6–8 months, at which time the plant is about 4 inches in height, and is then transferred to a one gallon container. After an additional 10–12 months of growth, the plant is about 11–13 inches in height and about 10–13 inches in spread. At this time, the plant is sufficiently large for commercial sale as a one gallon plant. If larger plants are desired for commercial sale, the plant can be re-potted from the one gallon container to a three gallon container. An additional 8–10 months of growth in the three gallon container is generally needed to produce a commercial three gallon container plant, at about 24–28 inches in height and 24–26 inches in spread.

Patent applications have been filed herewith for Azalea 'Crimson Princess', U.S. patent application No. 09/930,574, a dwarf form which originated as naturally occurring whole plant sport mutation of 'Crimson Majesty', and azalea 'Crimson Queen', U.S. patent application No. 09/930,575, a semi-dwarf form which originated as a naturally occurring branch sport of Azalea 'Crimson Princess'. The three "Crimson" azaleas have similar leaf coloration (187-A, 187-B, grayed purple group)(The foliage of 'Crimson Queen' is lighter than that of 'Crimson Princess' but darker that of 'Crimson Majesty' in appearance) and differ primary in growth size characteristics: 'Crimson Princess' being a dwarf (about 10–12 inches in height at about two ½ years from cutting), 'Crimson Queen' a semi-dwarf (about 16–18 inches in height at about 2½ years from cutting) and 'Crimson Majesty' being a standard (about 24–28 inches in height at about 2½ years). See FIGS. 8 and 9. By contrast, the parent stock 'Red Formosa' is a standard azalea (about 24–28 inches at two ½ years from cutting, with an ultimate height of 5–8 feet). All of the 'Crimson' hybrid azaleas have strikingly different foliage coloration (187-A, 187-B, grayed purple group) from the parent 'Red Formosa' (N189A grayed green group). ). See FIGS. 2 and 9.

SUMMARY OF THE INVENTION

The 'Crimson Majesty' new growth has a dominant reddish purple color in a rather wide border on the outer margin of the leaves. This color is overcome with green as the leaf matures, but the pigment remains slightly noticeable on the topside of the foliage. This gives the plant a purple or maroon color when it is viewed from a normal distance. The coloration is readily apparent when viewed in contrast next to green leaf azaleas or shrubs. The underside of the leaf retains more reddish purple pigment. The cultivar has the growth habitat of full size indica azaleas. The cultivar has a red-purple flower color similar to that of Azalea 'Red Formosa,' but the flower and flower color is not considered a novel feature.

The following are the most outstanding and distinguishing characteristics of this new cultivar when grown under normal horticultural practices in Independence, La.

1. The unique foliage coloration, color 187-A (grayed purple group).
2. Easily propagated with semi-hardwood cuttings in late spring through the summer.
3. Fast growth rate under normal fertilization and moisture conditions.
4. Upright, dense and globose in nature.
5. Good specimen plant.
6. Makes a good hedge or screen.

7. Very good foundation plant for large buildings or under high windows.

DESCRIPTION OF THE DRAWINGS

This new Azalea Hybrid variety distinguishing features are illustrated by the accompanying photographic prints in which.

Figure 1:
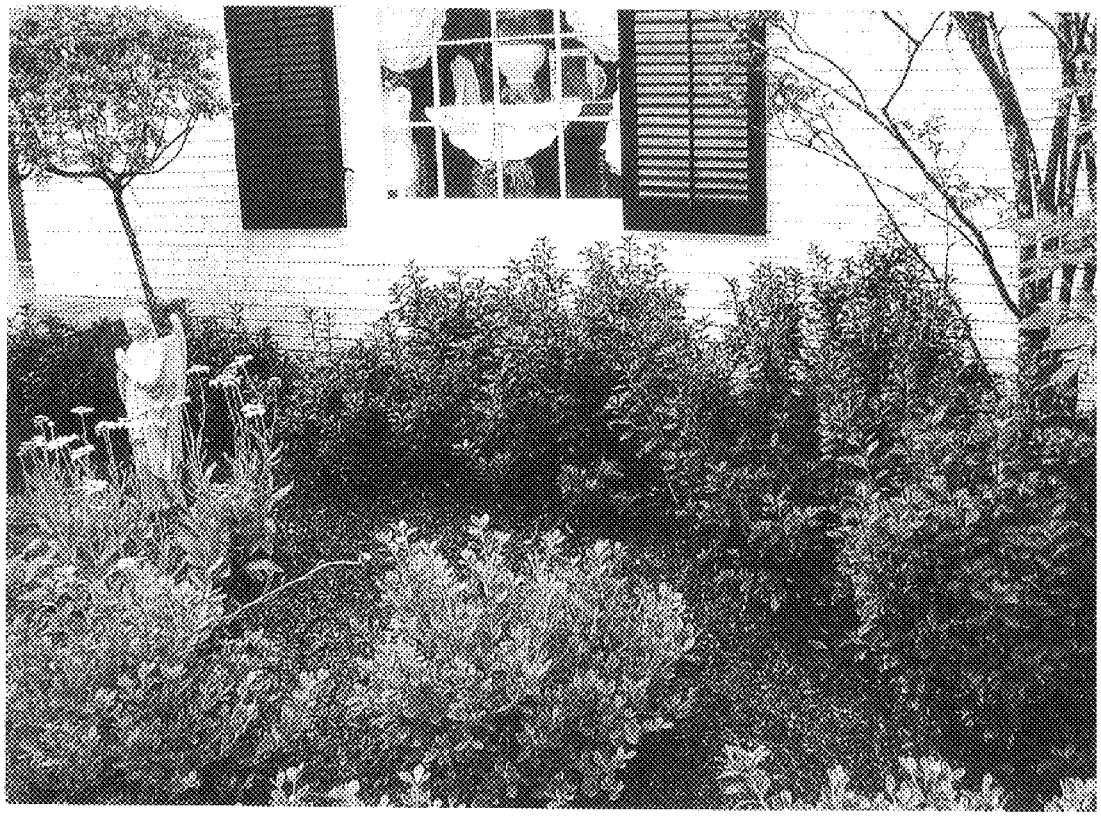
FIG. 1 is a view showing the "Crimson" varieties of azaleas' in place adjacent to the usual green colored leafed azaleas, demonstrating the difference in the plant's coloration to that of standard azaleas.
Figure 2:
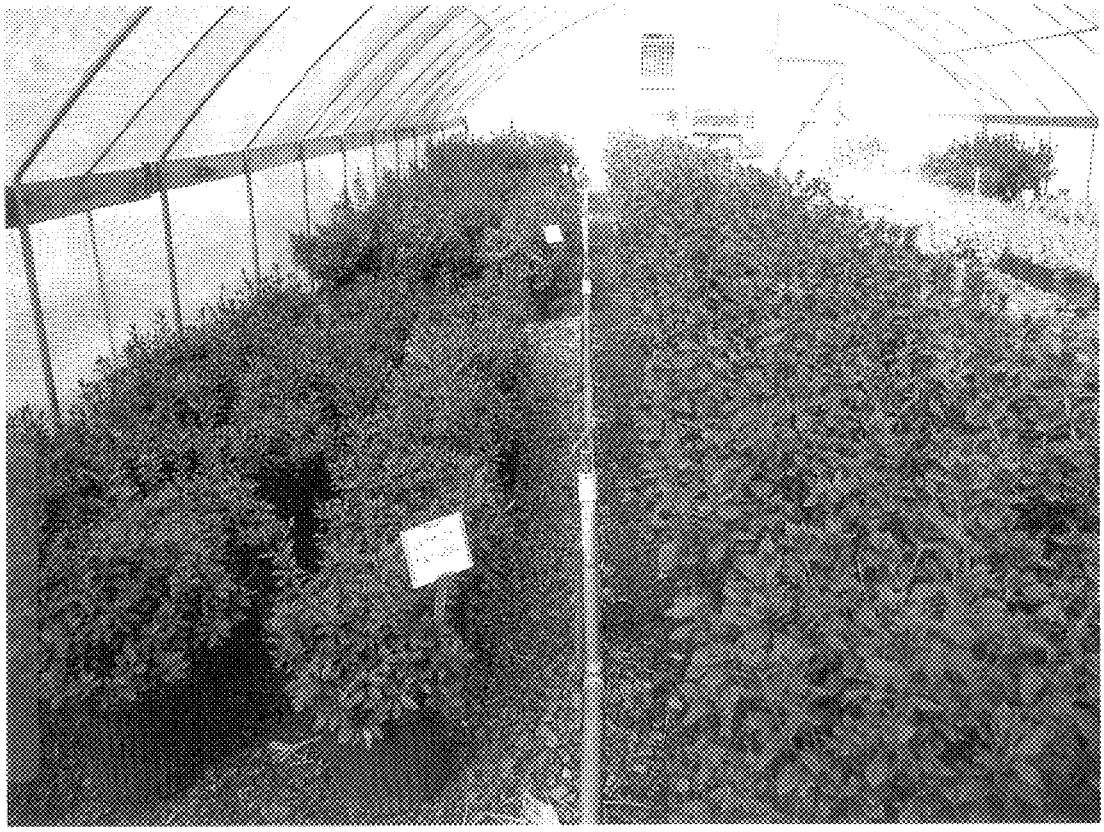
FIG. 2 is a view showing the "Crimson" varieties in filtered light adjacent to 'Red Formosa' azaleas. 'Crimson Princess' is in the foreground, 'Crimson Queen' in the middle ground, and 'Crimson Majesty' in the background left of the photograph showing the difference in coloration from 'Red Formosa.' All plants are approximately 2.5 years of age from cuttings.
Figure 3:
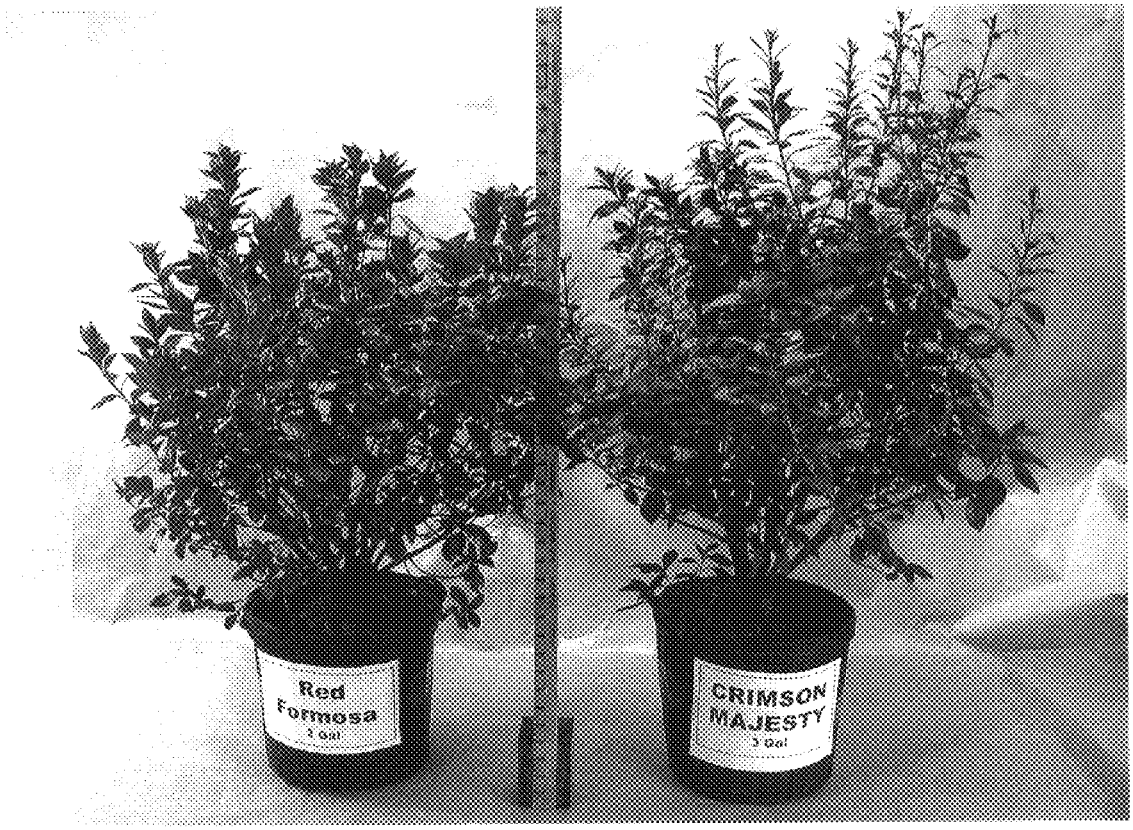
FIG. 3 shows the variety adjacent to the parent stock 'Red Formosa' of the "Crimson" line.

The colors shown are as true as is reasonably possible to obtain by conventional photographic procedures. The colors of the various plant parts are defined with reference to The Royal Horticultural Society Colour Chart. Description of colors in ordinary terms are presented where appropriate for clarity in meaning. Colors in the photographs may appear different than actual colors due to light reflectance. Color values cited in the Botanical Description of the Plant accurately describe the actual colors of the new Azalea.

DESCRIPTION OF THE PLANT 'CRIMSON MAJESTY'

The following is detailed description of the new variety of Azalea based on my observations made of plants grown in wholesale commercial production practices, in greenhouses, and in established landscape plantings in Forest Hill, La., and was compiled with the assistance of Dr. Lowell E. Urbatsch, Director of the LSU Herbarium, Louisiana State University.

Cultivar: 'Crimson Majesty', a full size standard indica azalea.

Botanical Description of the Plant

Scientific name: The plant belongs to a group of azaleas called the "Southern Indian azaleas" or "indicas" that are hybrids derived from various species of Rhododendron or derived directly from various species in that genus. *Rhododendron indicum* (L.) Sweet, although often given as the scientific name for this group of plants, has had little or no part in the parentage of the indica. Most indicas are descendents of *Rhododendron simsii* Planch. *R. mucronatum* G. Don and/or *R. pulchrum* Sweet or their hybrids; in the industry, however, the accepted parentage is that of *Rhododendron indicum.*

Growth habit: Shape of the plant at maturity: Broad compact, mound-forming shrubs. Individuals observed at about 3.5–4 years showed growth of approximately 36 inches tall and 36 inches broad or larger, these plants, however, have not been observed at maturity.

Branching habit: Sympodial (branching without a main axis but with many, more or less, equal laterals). One to several stems are evident at or near ground level that branch and re-branch frequently and at close intervals. Branches ascending or arcuate-ascending to upright. Branch characteristics (on mature growth of the current season): branch length, 10–15 cm; branch diameter, 2.5–3 mm; internode length, 1.5–10 mm.

Characteristics of the plant in winter dormancy: During the winter the plants are evergreen, i.e., the leaves remain on the stems. No signs of growth or flowering are evident during winter. No cold hardiness study has been conducted in colder climate zones. It was developed in the southern portion of zone 8 and has proved to be hardy in regard to the winter cold and summer heat.

Bark: Stem coloration on twigs is 178-B grayed-red group; bark coloration (on stems greater than 2 years old) is 177-B grayed-orange group. The stems, at least the lower ones, are rarely visible due to the compact leafy nature of the plants and, therefore, contribute little to its ornamental qualities.

Flowers:

Flower appearance: Corolla 5-lobed; star shaped; flaring open, 7–8 cm across (lobe tip to lobe tip); 4–5 cm deep; diameter at base of lobes is about 3 cm; corolla lobes slightly reflexed at or near about 1.5 cm back from lobe apices; corolla of a single whorl of petals, occasionally with 1–3 additional petals internal to the corolla.

Flower bud: Rate of opening just after bud corolla becomes visible is about 3 days but rate is variable with temperature, sunlight, and possible other conditions. Corolla color becomes visible when bud is about 12 mm long and 8 mm wide.

Flower bud shape is ovoid in shape when viewed dorsal-ventrally. In side view the bud bulges slightly outward while the inner surface is relatively straight. It is about 15 mm long and 10 mm wide when petals become visible and about 4 cm long when petals begin to open. As view from the top or in cross-section bud is slightly 5-lobed. Color of corolla in bud stages is near 60-B (Fan 2, Royal Horticultural Society Colour Chart).

Petals: The petals are 5 in number and basally fused; their appearance is satiny; texture is smooth. Petals are spatulate (obovate) and range from 4.5 to 5.3 cm long; lobes are rounded; margins are entire to slightly irregular, and they are somewhat undulate with about 8 undulations per cm giving the margin a crepe-like appearance.

External and internal petal color of the lobes is near 61-A (Fan 2, Royal Horticultural Society Colour Chart (compare with 'Red Formosa' petal color, at 64-B) and slightly darker toward corolla base i.e., 61-B (compare with 'Red Formosa' at 61-A). The anterior (uppermost) petal is somewhat mottled from base of lobe to base of petal; the spots are slightly darker being closest to 61-B, otherwise petal color is rather uniform.

Sepals: Sepals are fused basally forming a 5-lobed calyx. Each sepal is elliptic in shape and approximately 18 mm long and 5 mm wide with the lowermost 2–3 mm of each fused together forming a short calyx tube. Sepal margins is entire and the apex is acute. Sepals are moderately pubescent abaxially (outer surface) and glabrous adaxially (inner surface). Sepal color is close to 59-C on both inner and outer surfaces.

Peduncle: Peduncle (i.e., the stalk supporting a cluster of flowers) length is from 10–15 mm long and 2–2.5 mm in diameter; it is somewhat flexible and it provides strong support for the flower; it is moderately pubescent; and near 59-C in color.

Reproductive organs: Androecium consists of 9–10 stamens. Filaments are 3–4.5 mm long and about 1 mm in diameter; filament color is closest to 60-B; filaments are flexible and slightly shorter to slightly longer than the corolla tube. Anthers are 1.5–2 mm long; oblong in shape; and closest to 79-B in color; pollen is a creamy white, 155-D, and produced in moderate amounts. Gynoecium appears to consist of 5 fused carpels. The ovary is densely pubescent (sericeous) with the hairs obscuring ovary surface; hairs are shiny and closest to 60-C in color; ovary shape is ovoid and about 5 mm long. The style is about 6 cm long, typically slightly exerted, i.e., slightly longer than the corolla but it may be shorter in some flowers, about 1.5 mm in diameter, and near 60-B in color. The stigma is truncate (i.e., having a flat surface) to slightly concave, about 1.5 mm in diameter, and slightly 5 lobed in end view.

Leaves:

*Arrangement.*—Leaves alternate, that is one leaf per node. Leaves spaced about ¼ to ¾ inches apart along the stems. Leaf stalk (petiole) about ⅜ to ¾ inches long.

*Shape.*—Leaves elliptic to oblanceolate in outline; apices acute to acuminate; bases cuneate to rounded. Margins entire although somewhat ciliate.

*Size.*—½ to 1.5 inches broad and 1.5 to 3.5 inches long including the petiole.

Figure 9:
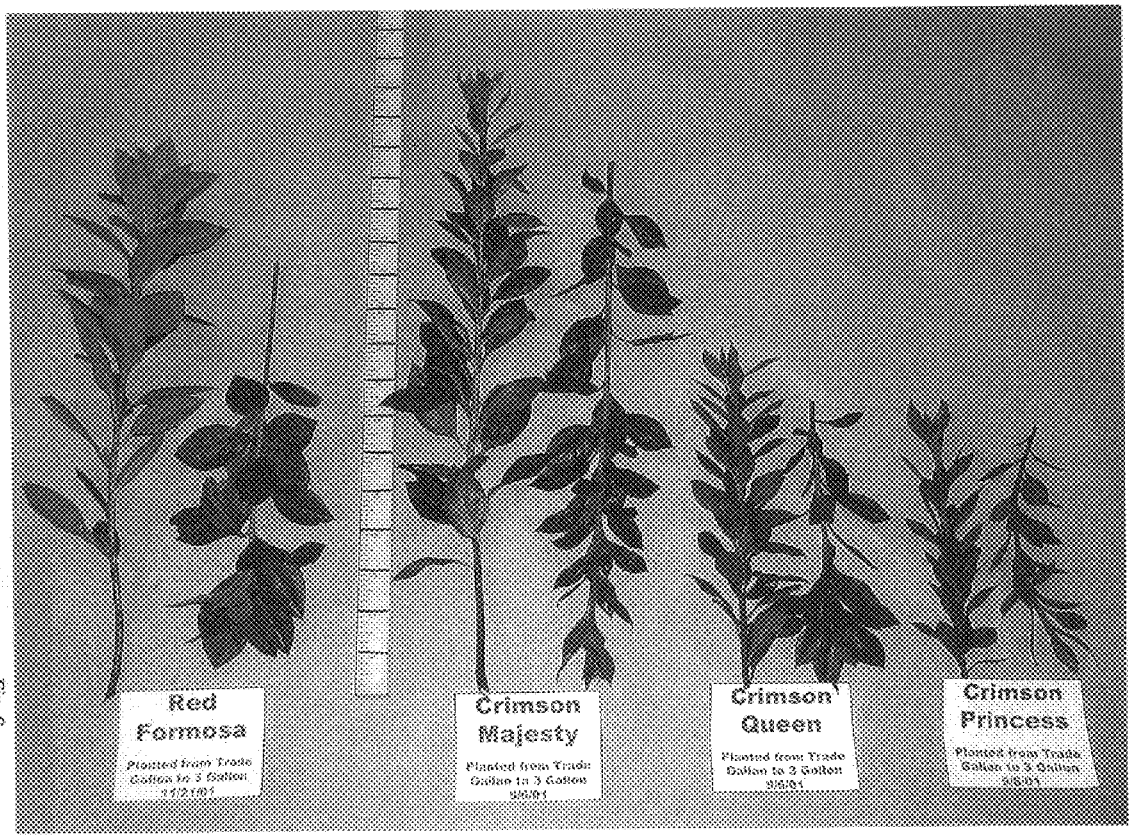
FIG. 9 stems with foliage from all three "Crimson" variety of plants adjacent to stems of 'Red Formosa'.
Figure 10:
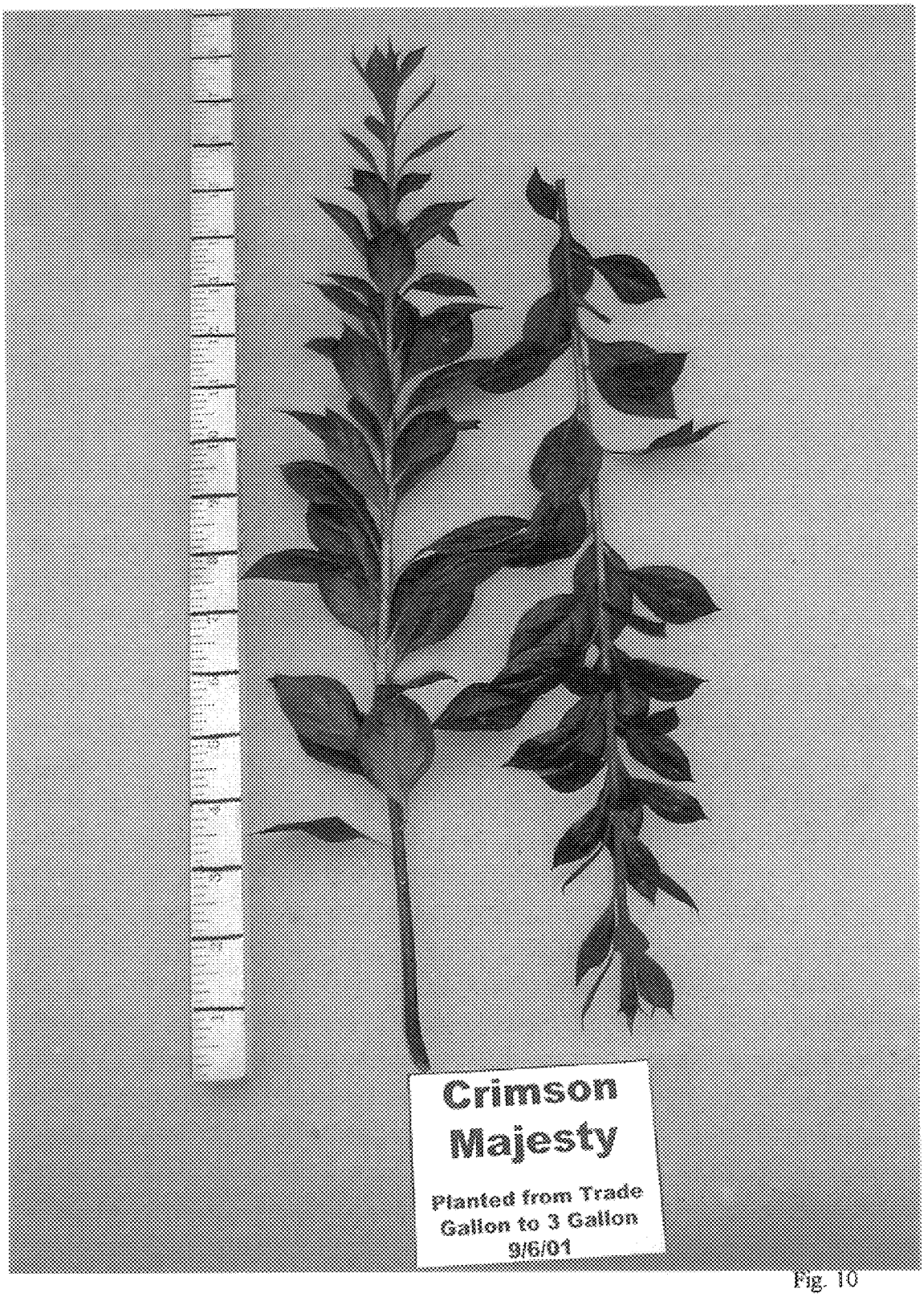
FIG. 10 show a close up of the stem and leaf structure of the instant variety showing the coloration.
Figure 11:
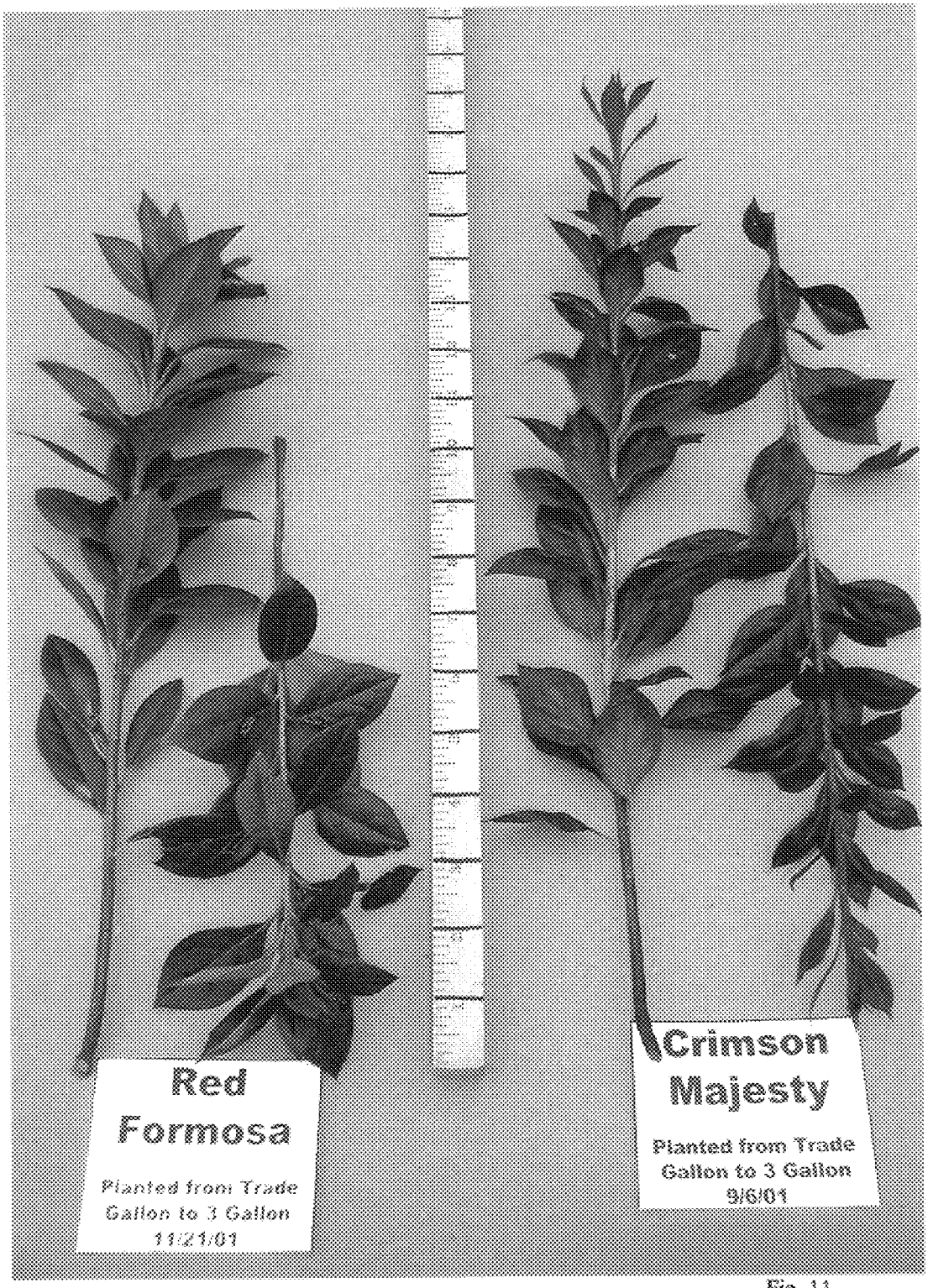
FIG. 11 show a close up of the stem and leaf structure of the instant variety showing the coloration in contract to that of the parent, 'Red Formosa'.
Figure 12:
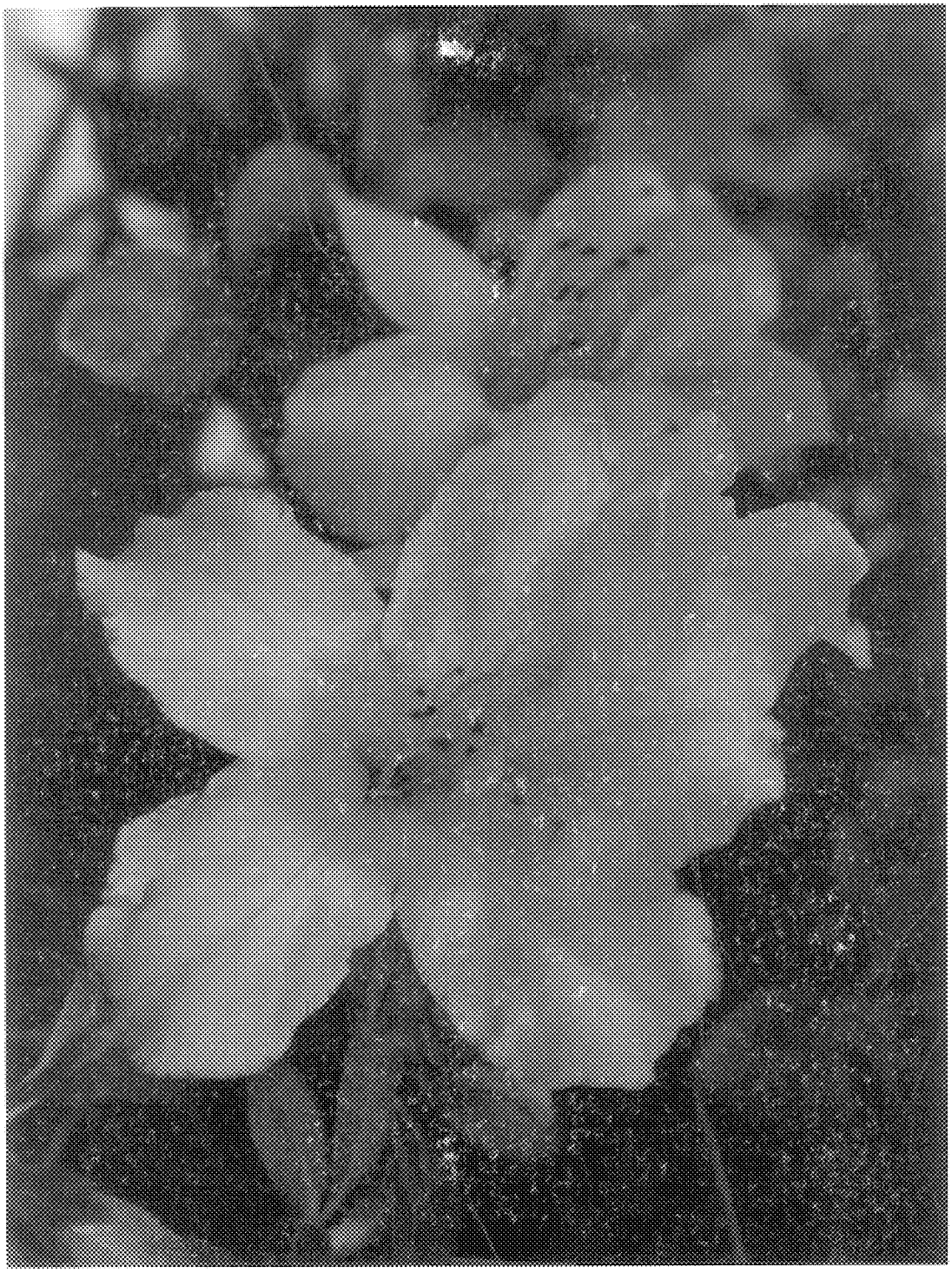
FIG. 12 shows a close up of a flower from the 'Crimson Majesty' variety.
Figure 13:
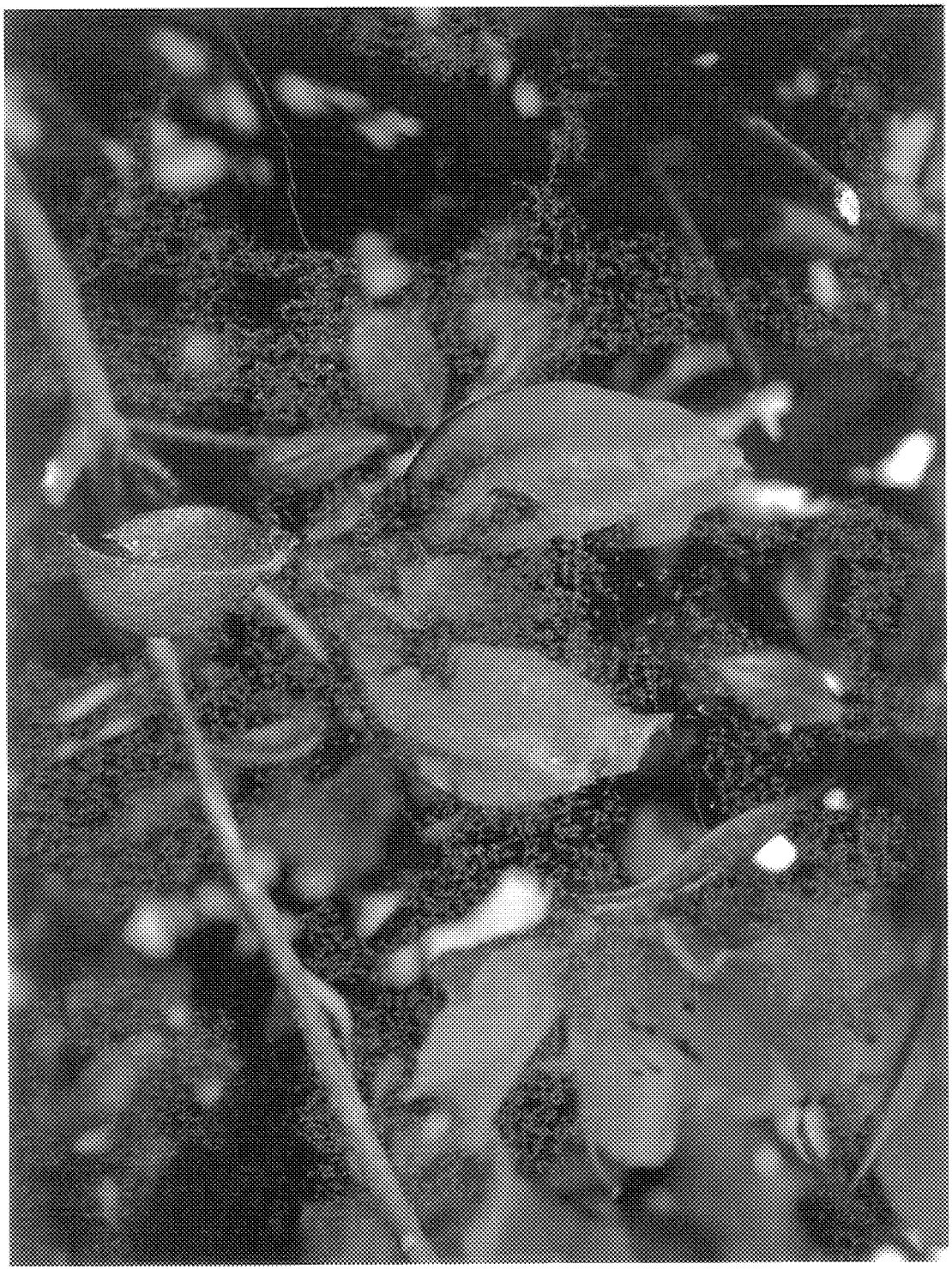
FIG. 13. shows a bud from the 'Crimson Majesty' variety.
Figure 14:
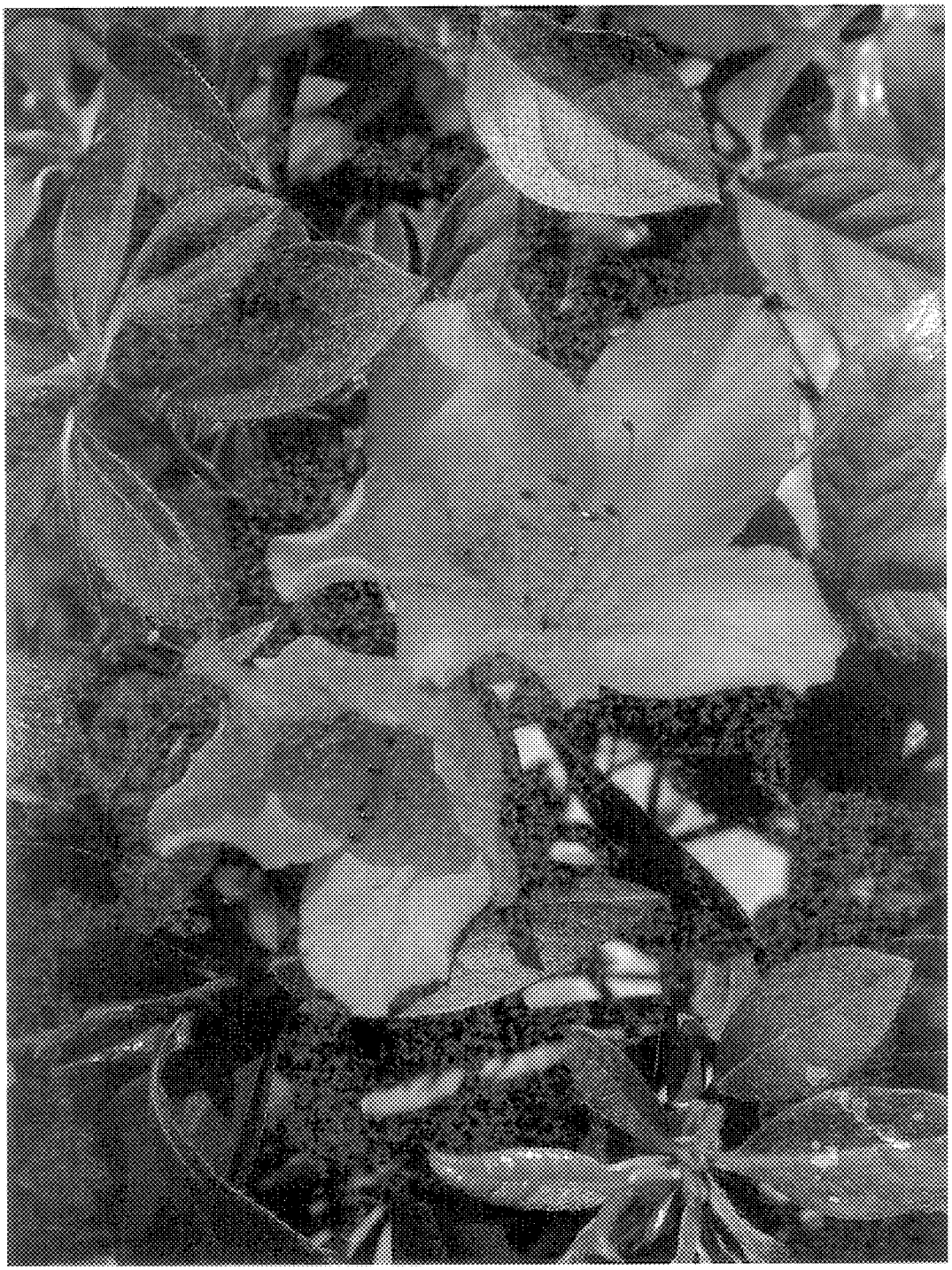
FIG. 14 shows a close up of a flower from the 'Red Formosa' variety.
Figure 15:
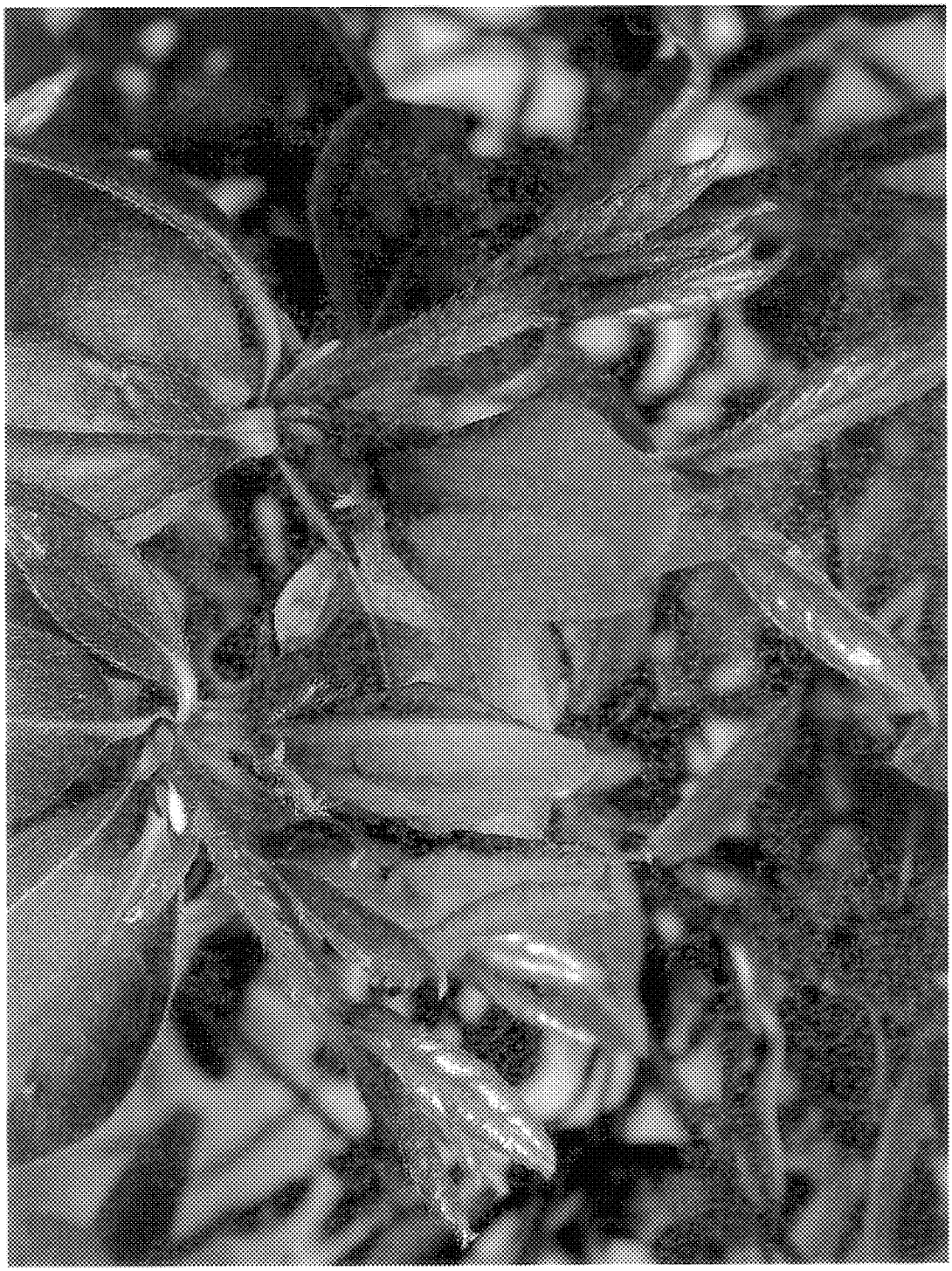
FIG. 15 shows a close up of a bud from the 'Red Formosa' variety.

*Color.*—Crimson on the upper and lower surfaces; shades of green somewhat more evident on the upper surface, less so on the lower (see accompanying Table 1). The crimson color is more intense on the new foliage and diminishes somewhat as the leaves age resulting in the older foliage having a deep crimson/green hue. In the 'Crimson Majesty' there is a tendency for some of the leaves to have bright green splotches along the midvein or occasionally on other areas of the leaves. Leaf color in this variety differs significantly from standard 'Red Formosa' which has bright green foliage at all stages of maturity. See FIGS. 9 and 11. Veins, especially the midvein and secondary veins, on the underside of the leaves on the 'Crimson Majesty' retain the crimson color at all stages of development. See FIG. 10.

The Royal Horticultural Society Colour Charts were used as per their instructions in order to better quantify the colors of the leaves. The results are summarized in the following Table 1.

TABLE 1

| Age of leaves | Feature | RHS color group | Best color match | Variation among leaves |
|---|---|---|---|---|
| Newly formed leaves | Upper surface[1] | Greyed-Purple Group | 187-A | 139-A, Green Group[1] |
| | Lower surface | Greyed-Purple Group | 187-C | 187-D, Greyed-Purple Group |
| | Veins, lower surface | Greyed-Purple Group | 187-C | 187-D |
| Mature leaves | Upper surface[2] | Greyed-Purple Group | 187-B | 136-A, Green Group |
| | Lower surface[2] | Greyed-Purple Group | 184-B | 137-B, Green Group |
| | Veins, lower surface | Greyed-Purple Group | 187-B | — |
| | Splotches along midveins on upper surface | Green Group | 136-B | — |
| | Splotches along midveins on lower surface | Green Group | 137-B | — |

[1]In 'Crimson Majesty' the green shades are somewhat evident in the young leaves, but more evident in the mature leaves.
[2]The mature leaves appear to be a blending of the green and reddish colors resulting in the greyed purple color.

Figure 4:
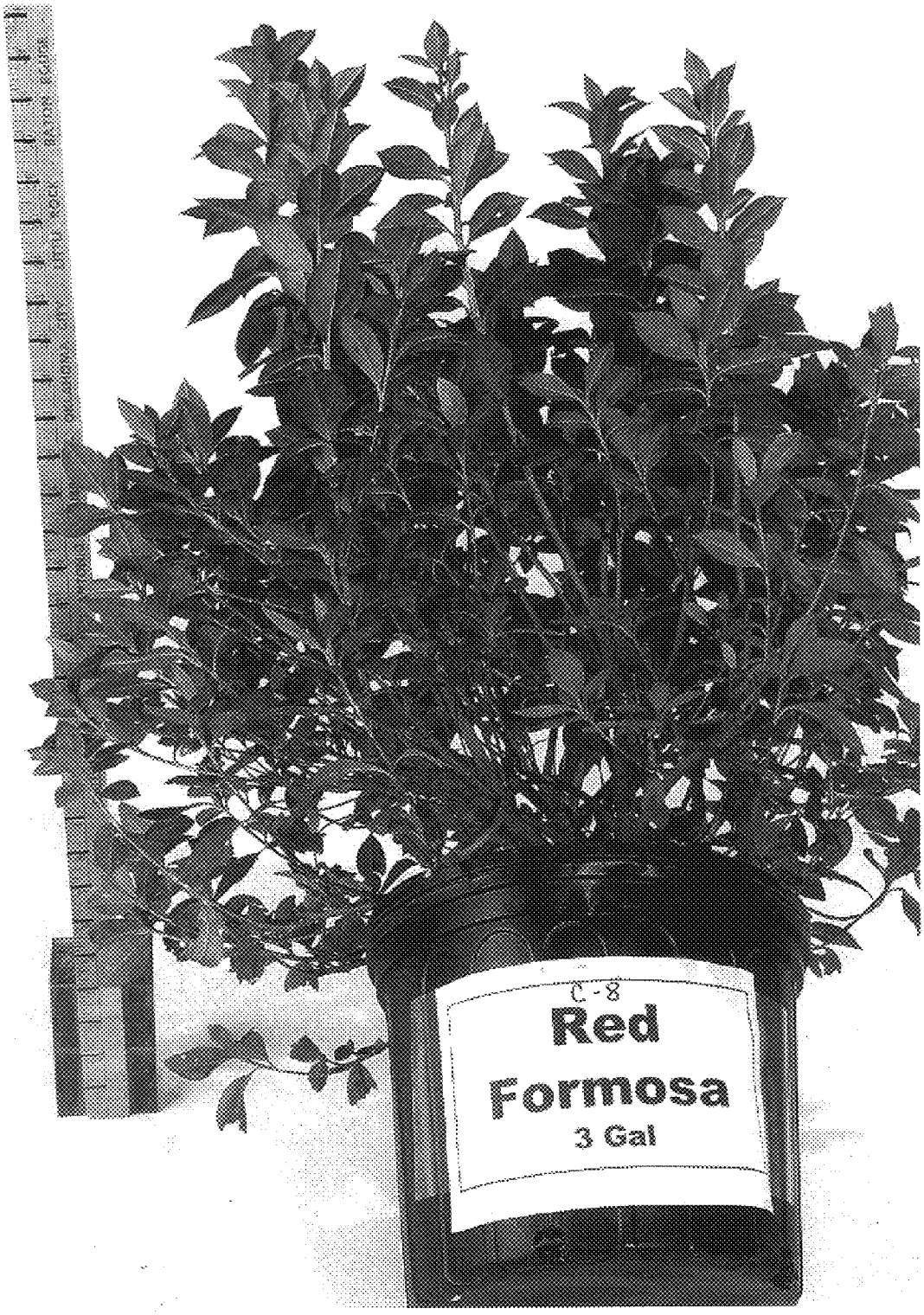
FIG. 4 shows the foliage and stem color of the underside of the foliage of 'Red Formosa' the parent stock of the 'Crimson' varieties.
Figure 5:
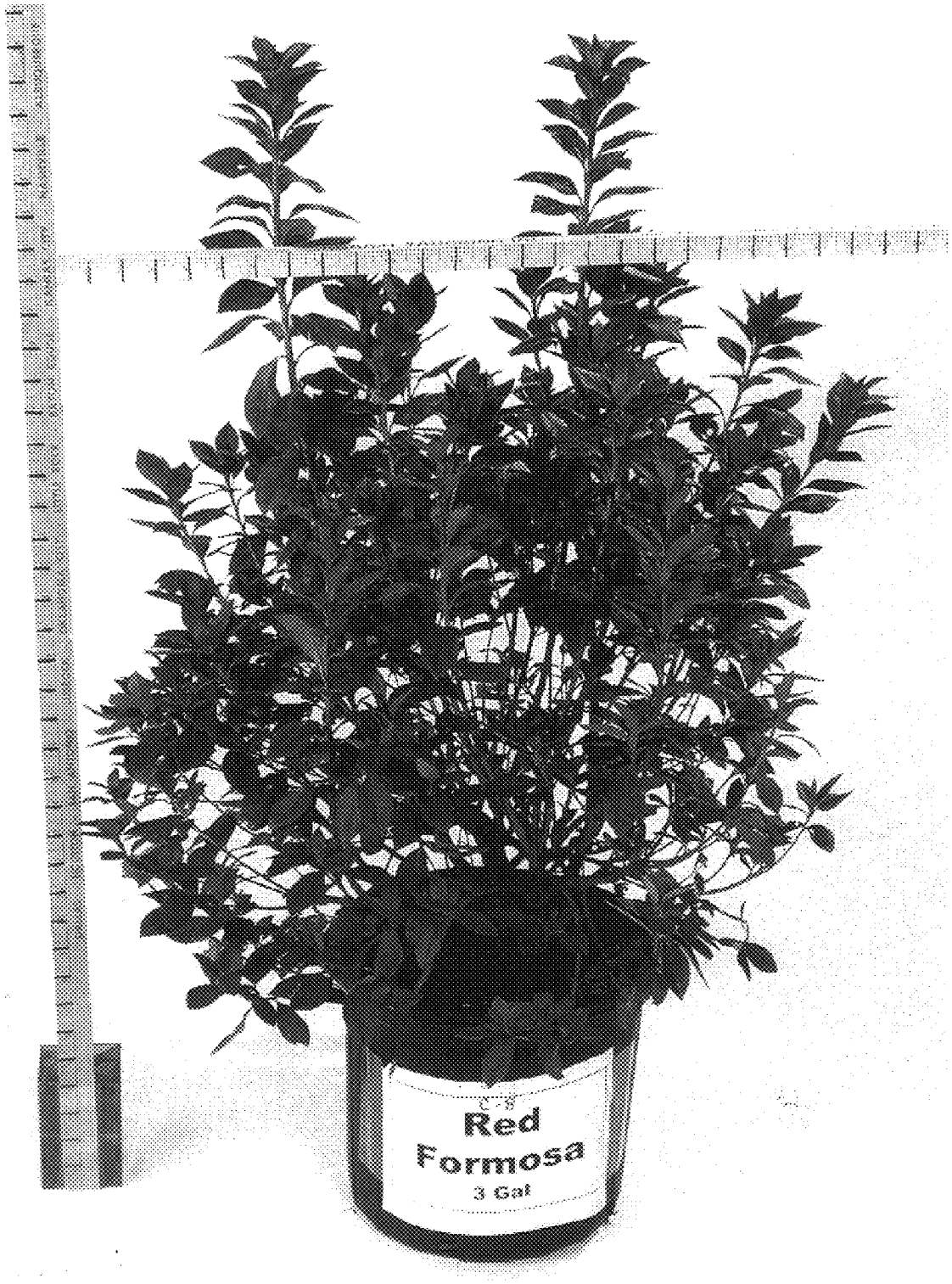
FIG. 5 shows the foliage and stem color of the upper surface foliage of 'Red Formosa' the parent stock of the 'Crimson' varieties.
Figure 6:
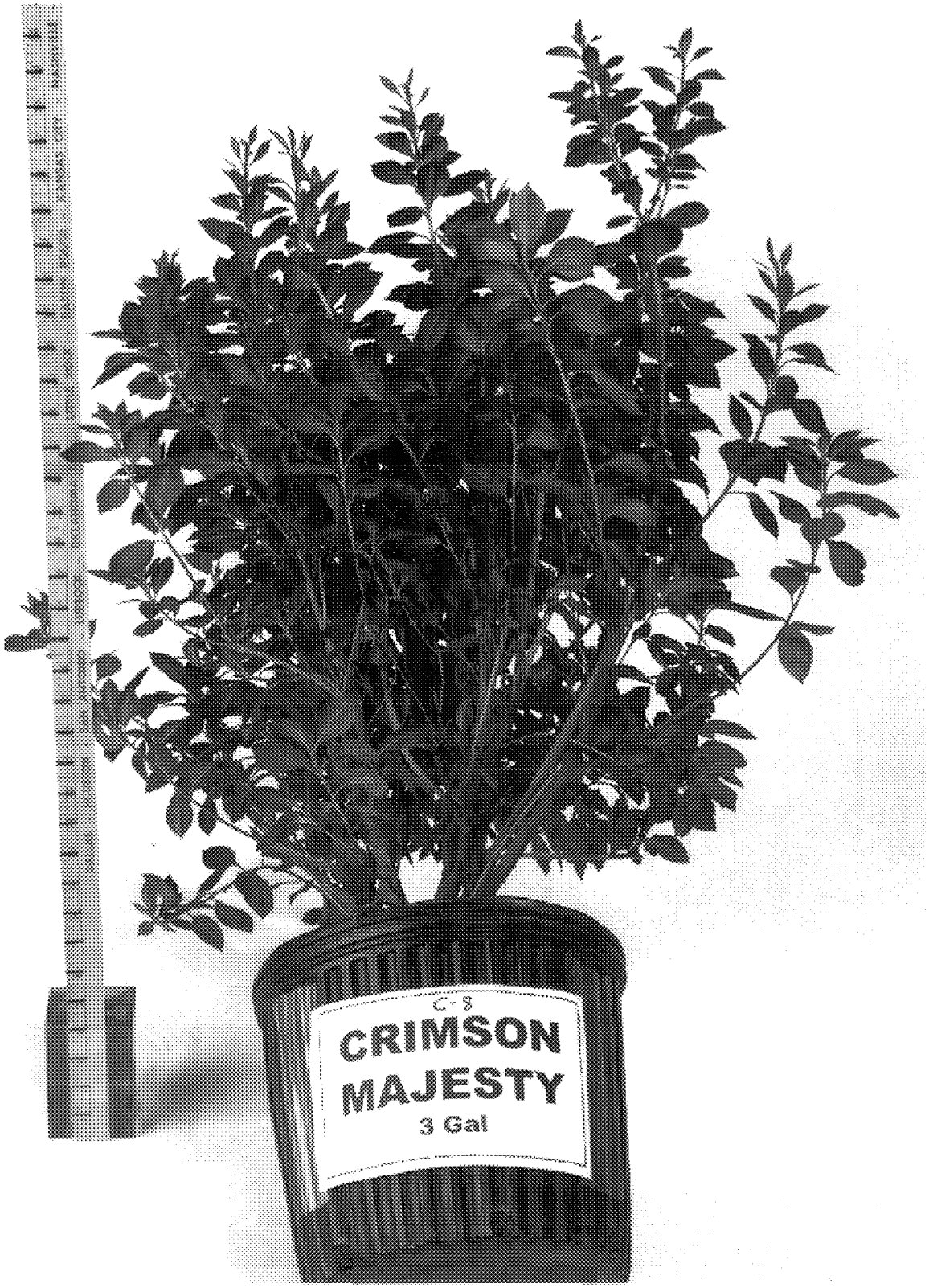
FIG. 6 shows the growth habit of a three gallon plant 2.5 year old plant and showing the foliage and stem color of the underside of the foliage of the instant variety.
Figure 7:
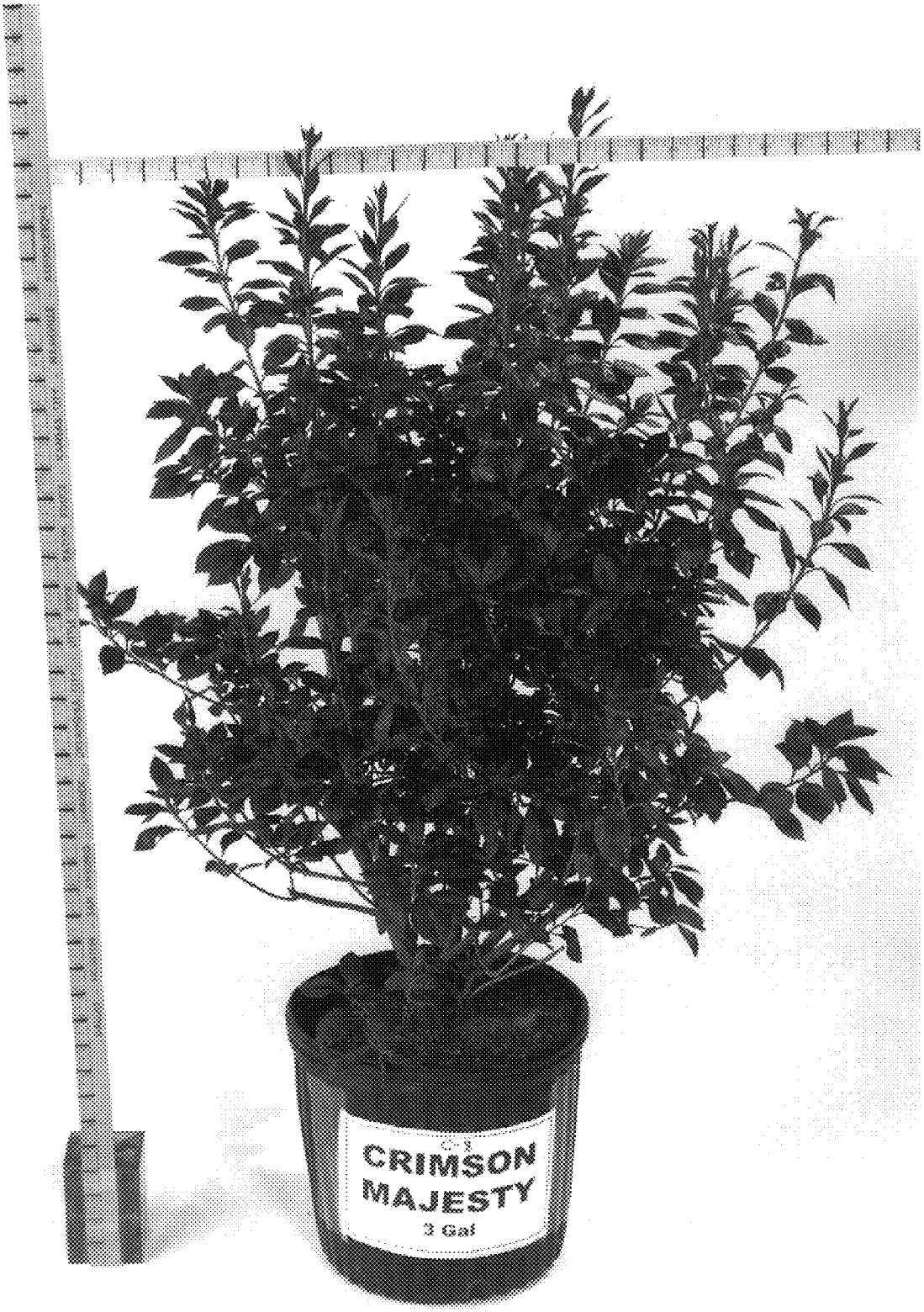
FIG. 7 shows the growth habit of a three gallon plant 2.5 year old plant and showing the foliage and stem color of the upper surface foliage of the instant variety.
Figure 8:
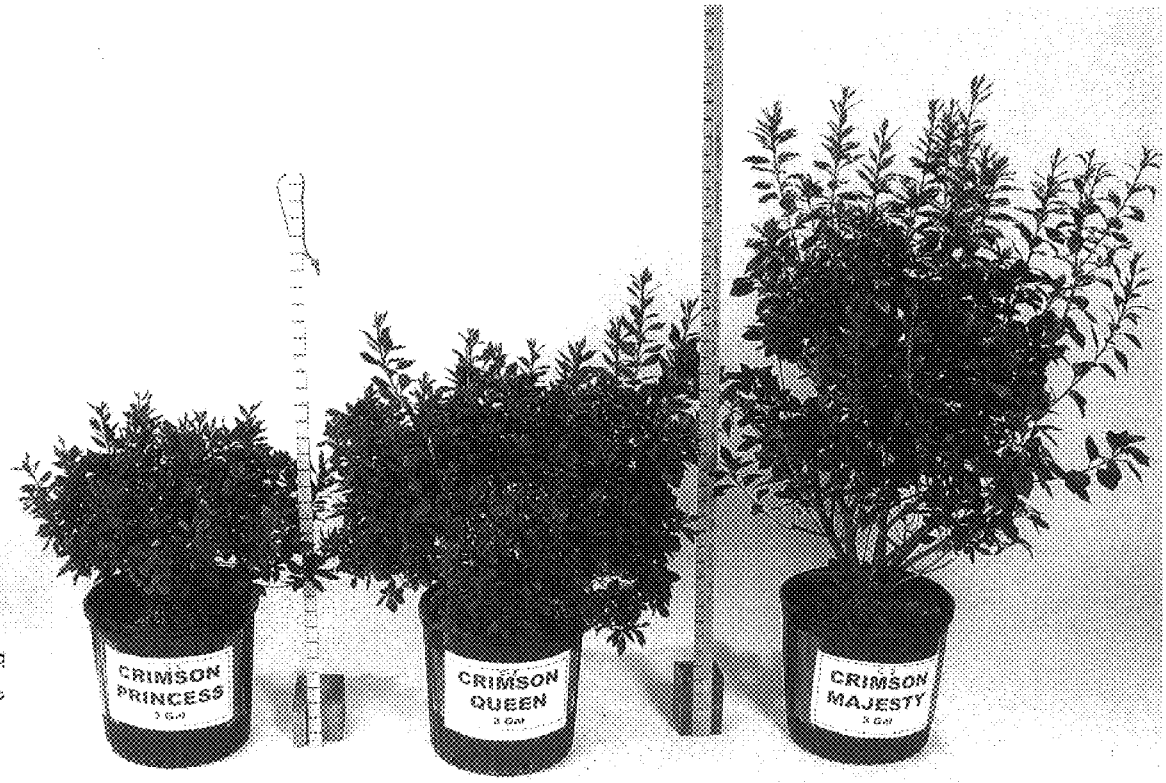
FIG. 8 shows the three "Crimson" variety plants adjacent each other to show the distinction in plant growth characteristics, all plants being about 2.5 years of age from cuttings in a three gallon container.

As a comparison, coloration of 'Red Formosa' is as follows: leaves upper surface, grayed-green group, N189A; leaves lower surface, green group, 138A; stem coloration 138-B Green group; bark coloration, 177-B Grayed-orange group; petiole coloration 138-B, 138-C Green Group. See FIGS. 4 and 5.

Indumentum: The indumentum or plant hairs (trichomes) are hirsute in nature, i.e. the individual hairs are uniseriate, slender, tapering at the tip and arising more or less perpendicular to the epidermis, and becoming somewhat flexuous slightly above the leaf surface. The hairs give the leaves and twigs a somewhat bristly texture. The same type of hairs are present on both the upper and lower leaf surfaces. In terms of density the indumentum is characterized as being moderately pubescent with the hairs being spaced about 1/32 inch (0.5 mm) apart. On the lower surface the hairs are somewhat more closely spaced along the veins and petioles. Indumentum on the stems is similar except for the hairs being somewhat more closely spaced than on the leaf blade surfaces.

Fruit: None apparent.

Other:

*Petiole.*—Length 5–10 mm; diameter 1.5–3 mm wide, 1.5 mm thick; coloration upper and lower surfaces, 59-A red purple group with flecks of 59-A green group.

*Fragrance.*—Insignificant — None apparent.

*Taste.*—Not relevant.

*Disease resistances.*—No known Azalea diseases observed to date on plants grown under commercial conditions. Expected to be similar to 'Red Formosa' cultivars — resistant to flower and leaf gall, caused by exobasidium vaccinii and root rot caused phytophthora cinnamomi; susceptible to Lace bug and to petal blight caused by ovulinia azalea.

*Seed production.*—Seed production has not been observed.

*Vigor.*—Similar to 'Red Formosa' cultivars, hardy in zones 7–9.

I claim:

1. A new and unique variety of Azalea plant named 'Crimson Majesty' as herein shown and described.

* * * * *